US00PP08658P

United States Patent [19]

Tustin

[11] Patent Number: Plant 8,658

[45] Date of Patent: Mar. 29, 1994

[54] CRABAPPLE VARIETY NAMED SCIORN

[76] Inventor: Donald S. Tustin, 14A Lovat Street, Havelock North, New Zealand

[21] Appl. No.: 945,070

[22] Filed: Sep. 14, 1992

[51] Int. Cl.[5] ..... A01H 5/00

[52] U.S. Cl. ..... Plt./35.2

[58] Field of Search ..... Plt. 35.2

[56] References Cited

PUBLICATIONS den Boer, A. F. (descriptions of) "*Malus sieboldii*" *Ornamental Crab Apples,* 1959, American Association of Nurserymen, pp. 20, 21, 168 and 169.

Application for Plant Variety Rights.
Objective Description of Variety.
New Zealand Plant Variety Rights Journal, No. 47, Jul.-Sep. 1991, pp. 5-7 (14 Oct. 1991).

*Primary Examiner*—James R. Feyrer
*Attorney, Agent, or Firm*—Quarles & Brady

[57] ABSTRACT

This invention relates to a new and distinct variety of crabapple tree which was selected from a rootstock breeding progamme at Appleby Research Orchard, Nelson, New Zealand. The new variety is designated Sciorn. The variety is characterized by very small brightly colored orange-red fruit.

4 Drawing Sheets

SUMMARY OF THE INVENTION

The invention relates to a new and distinct variety of crabapple tree which was selected from a seedling population of *Malus seiboldii* in a rootstock breeding programme, Appleby Research Orchard, Nelson, New Zealand. The new variety is designated "Sciorn".

The seed parent of the new variety is *Malus seiboldii.* The pollen parent is unknown.

Accessions of Asiatiac Malus species were obtained from Japan. Accession No. 32 was obtained from the Morioka Research Station Japan. Accession No. 32 was *Malus seiboldii.* A considerable number of seedlings from this accession proceeded beyond primary disease screening for resistance to root rots. Over a period of 20 years several selections from Accession No. 32 were noted as having some ornamental potential. This evaluation was subjective. Sciorn was selected and registered on the basis of most potential. Sciorn was selected on the basis of tree form, regular flowering, freedom from powdery mildew disease, lack of severe disfigurement by apple scab (Venturia), and the spectacular characteristic of fruiting profusely on all aged wood with persistence of fruit until it is softened enough for birds to eat seeds in late winter or by abscision induced by bud break.

The new variety is distinguished from other ornamental malus varities by small oblate, orange-red persistent fruit, retained for most of the winter. These fruit are a major ornamental feature of the selection providing winter-long red colour in a deciduous tree which is not typical of many ornamental malus. Other distinguishing characteristics are profuse annual flowering, with a mass of pure white, flat-formed single florets opening from pale-pinked tinged buds. Flower is a burst of pure white flowers covering the whole tree simultaneously and lasting only about a one week.

The new variety is reproduced by vegetative propagation on MM106 root stock. The unique combination of characteristics come true to form and are established and transmitted through succeeding propagations.

BRIEF DESCRIPTION OF THE PHOTOGRAPH

The accompanying photograph shows as nearly true as it is reasonably possible to make the same in a colour illustration of this character typical specimens of fruit and flowers of the new variety.

FIG. 1: shows typical specimens of the fruit of the variety of the tree.

FIG. 2: shows typical specimens of the flowers of the variety.

FIG. 3: shows typical specimens of the leaves of the variety.

FIG. 4: shows the habit of the variety in dormancy.

DETAILED DESCRIPTION

The specimens described in detail below were grown at Havelock North, New Zealand. The observations were made in 1984 to 1989 on trees which were three year to ten years old. The colours are according to the Pantone Colour Formula Guide 747XR.

Tree: Medium vigour; drooping spreading habit; predominance of bearing on shoots; colour of Bark (mature) mid brown (464U).

Figure 4:
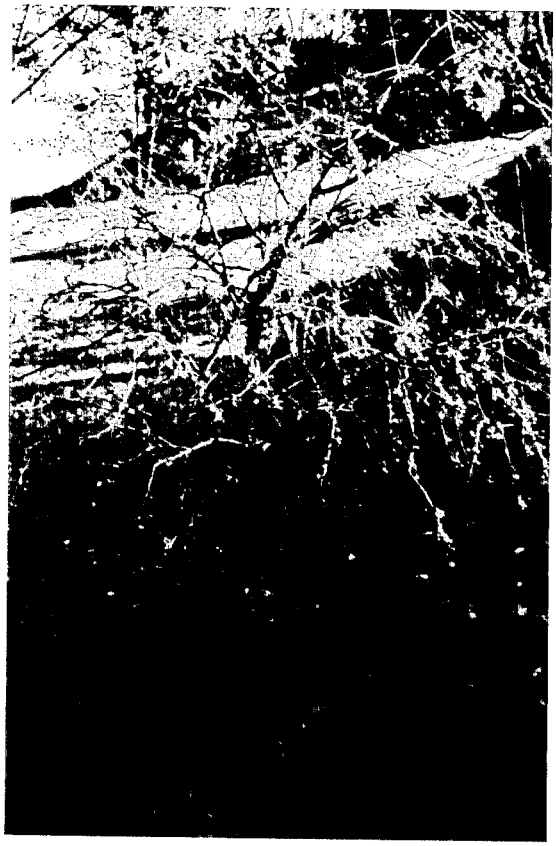

The oldest specimen is seven years old on its own roots. The vigor is weak to moderate. Approximately 30–40 cm of terminal growth was achieved in its seventh year. The height is 3.5 meters and the spread 3 meters. The shape of the tree is widely pyramid to round. There is no dominant leader. There are 4–5 steeply branched main limbs producing a small tree rather than a bush. It has an acrotonic growth habit to give a semi-weeping habit (i.e., the crotch angles of lateral branches of main stems are typically 30° from the vertical). FIG. 4 shows a seven year old tree on its own roots in dormancy.

Trunk: Bark smooth; few cracks.

Dormant one year old shoot: (observed in winter on trees at least three years old) thickness (diameter at centre of middle internode), thin; number of lenticels, few; the size of the bud is very large in relation to the shoot diameter; dormant fruit bud shape (on spurs), conical-ovoid.

Branches: Medium density; smooth.

Figure 3:
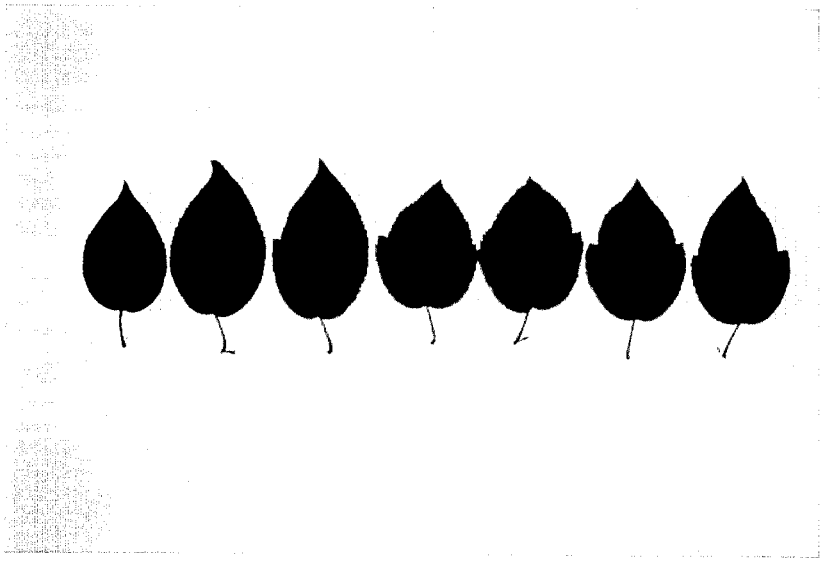

Leaves: Length, 80 to 100 mm; width 45 to 60 mm; large size; outward pose; medium length/width ratio of blade; up-folded shape in cross-section; serrate indentation of margin; strong glossiness of upper side; weak pubescence on lower side; long petiole length; small stipule size; early time of bud burst; colour of expanding leaf blade, green; lobes, sometimes present; colour of upper side, dark green (350C); anthocyanin coloration of upper side, absent; colour just before leaf fall, yellow. Sciorn displays fewer load leaves than the seed parent *Malus seiboldii. Malus seiboldii* "Toringo crab" displays large broad lobes while the lobing of Sciorn leaves may be single, single pair, or no lobes. The range of lobing in Sciorn is depicted in FIG. 3. Leaf fall occurs at mid-autumn, in the first to third week in May in Hawkes Bay, New Zealand. The leaf veins are green-white on both the underside and upper side. The mid-ribs have a red pigmentation at the basal region changing to green-white at the apical end. The leaf petiole is also red.

Figure 2:
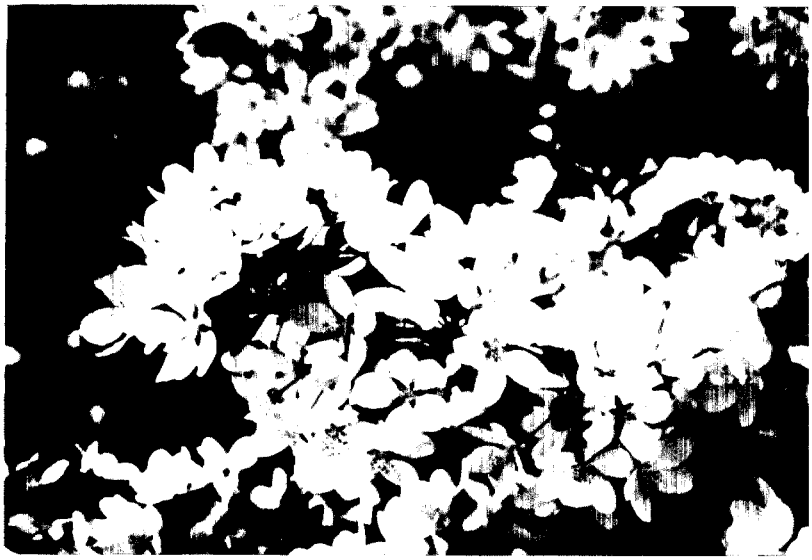

Flower: FIG. 2 depicts the flowers of Sciorn. (Unopened flower observations made on second or third flower bud when the terminal flower is opening. Observatoins are made at the start of anther dehiscence on an average of ten second or third flowers with intact pedicels). Medium size (diameter with petals pressed flat); moderately cupped shape opening to flat shap; margin of petals free; petal colour of upper side — Pantone Colour guide, pure white; petal colour of lower side — Pantone Colour Guide, pure white; medium time of beginning of lowering (10% flowers); colour of bud just before flower opens, pink; type, single; Pedicel colour, green; approximate date of flowering, mid-spring; flowers open between September 25 and October 2 in Hawkes Bay. Pollen shed occurs 2–3 days after anthesis.

Type: Single.

Figure 1:
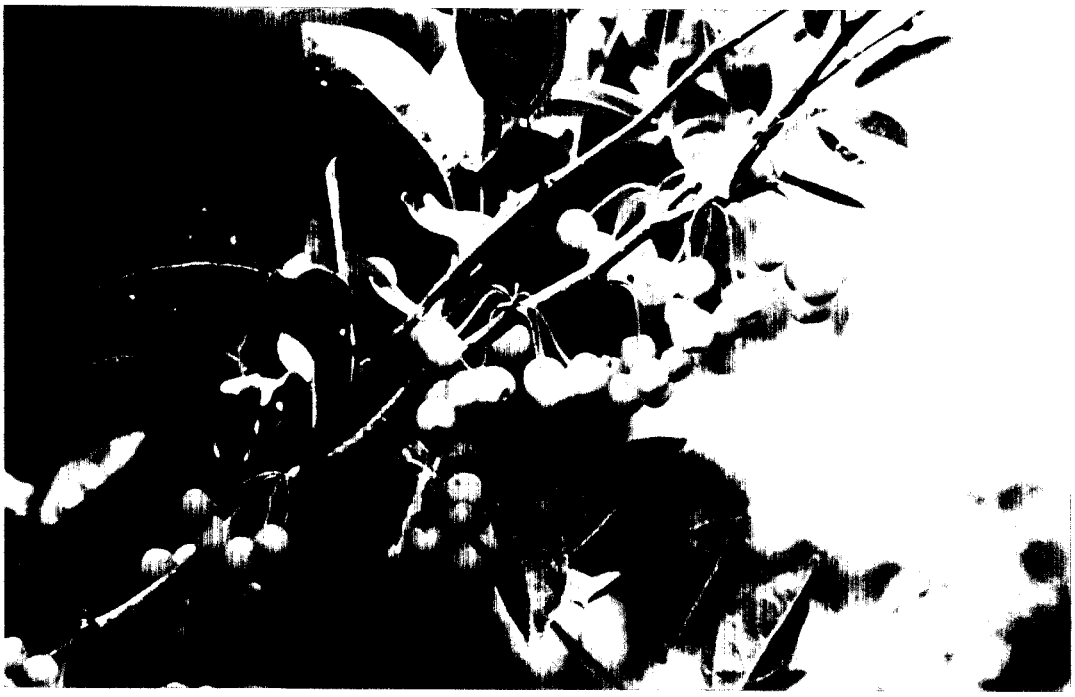

Fruit: FIG. 1 shows the fruit of Sciorn on the tree.

*Size.*—Very small; length 11 mm to 14 mm; breadth 14 mm to 18 mm.

*Shape.*—Short cylindrical (oblate); symmetrical in side view; ribbing absent; weak crowning at distal end.

*Cavity.*—Shallow depth; broad width.

*Basin.*—Medium depth; broad width.

*Locules.*—4–6, with 5 being common.

*Stem.*—thickness 1 mm; length, 30–40 mm.

*Calyx tube.*—Long length; narrow width; shape, Y-shaped; persistence of calyx, absent.

*Sinus.*—Closed.

*Eye.*—Size, large; aperture, closed.

*Distinctiveness of core-line.*—Weak when examined in cross-section (median through locules).

*Aperture of locules.*—Closed when examined in cross-section.

*Central cavity (in cross-section).*—Absent.

*Skin.*—Relief of surface, smooth; bloom of skin, present; greasiness of skin, absent, translucency of skin, present; thickness of shin, thin; red groud colour; cracking tendency of skin, absent.

*Over-colour.*—Overall present percentage of over-colour of skin, orange to red colour (187C); solid flush; russet absent or very low.

*Lenticels.*—Size, small.

*Flesh.*—Colour, yellowish/gold (128C); texture, fine.

*Flavour.*—Inedible, highly astringent.

*Persistence.*—Very long.

*Fruit setting.*—Very many.

Time of leaf fall: Medium.

Seed: Dark brown (469C). The suitability of Sciorn as a root stock is limited due to problems with compatibility with *Malus domestica.*

What I claim is:

1. A new and distinct variety of crabapple plant substantially as herein described and illustrated, and identified by the characteristics enumerated above.

* * * * *